United States Patent [19]

Diem et al.

[11] 3,991,118

[45] Nov. 9, 1976

[54] PRODUCTION OF FORMALDEHYDE

[75] Inventors: Hans Diem, Mannheim; Guenther Matthias; Friedrich Brunnmueller, both of Ludwigshafen, all of Germany

[73] Assignee: Badische Anilin- & Soda-Fabrik Aktiengesellschaft, Ludwigshafen (Rhein), Germany

[22] Filed: Mar. 20, 1972

[21] Appl. No.: 236,210

[30] Foreign Application Priority Data

Apr. 7, 1971 Germany............................ 2116947

[52] U.S. Cl............................ 260/603 HF; 260/606
[51] Int. Cl.$^2$......................................... C07C 45/16
[58] Field of Search............................ 260/603 HF

[56] References Cited
UNITED STATES PATENTS

| | | | |
|---|---|---|---|
| 1,738,745 | 12/1929 | Weith et al. .................. | 260/603 HF |
| 1,744,295 | 1/1930 | Ahlbeck ....................... | 260/603 HF |
| 2,883,426 | 4/1959 | Brackman..................... | 260/603 HF |
| 3,444,216 | 5/1969 | Parikh et al. ................. | 260/603 HF |

FOREIGN PATENTS OR APPLICATIONS

| | | | |
|---|---|---|---|
| 1,576,568 | 6/1969 | France.......................... | 260/603 HF |
| 539,488 | 9/1941 | United Kingdom .......... | 260/603 HF |

OTHER PUBLICATIONS

Walker, Formaldehyde, 2nd Edit., 1953, pp. 65, 66, 393 and 394.
Clark, Modern Organic Chemistry, 1964, pp. 238–239.
Oguri et al., Chemical Abstracts, vol. 45, Col. 10436e, 1951.

*Primary Examiner*—James O. Thomas, Jr.
*Assistant Examiner*—G. T. Breitenstain
*Attorney, Agent, or Firm*—Johnston, Keil, Thompson & Shurtleff

[57] ABSTRACT

Production of formaldehyde by oxidizing dehydrogenation of methanol in the presence of a silver catalyst and a tertiary or secondary amine. The formaldehyde which can be prepared by the invention is a disinfectant, tanning agent, reducing agent and valuable starting material for the production of synthetic resins, adhesives and plastics.

5 Claims, No Drawings

PRODUCTION OF FORMALDEHYDE

The invention relates to a process for the production of formaldehyde by oxidizing dehydrogenation of methanol in the presence of a silver catalyst and a tertiary or secondary amine.

In the production of formaldehyde in the presence of silver catalysts (Ullmanns Encyklopadie der technischen Chemie, volume 7, pages 659 et seq) byproducts such as formic acid, carbon monoxide and carbon dioxide are formed. Among these impurities the acid is particularly undesirable because it causes corrosion and is troublesome in further processing. The formaldehyde obtained is as a rule absorbed in water to form a 28 to 50% by weight solution. When these solutions are stored, further formic acid is formed, the rate of formation of the same being increased by increased concentration of acid. Furthermore other reactions may take place during storage, such as polymerization and Cannizzaro reaction of the formaldehyde and the formation of formaldehyde dimethyl acetal, according to prevailing conditions (Ullmann, loc.cit., page 667; Walker, Formaldehyde (Reinhold Publ. Corp., New York, 1964), pages 93 to 98). A 37% by weight untreated aqueous formaldehyde solution generally contains from 0.003 to 0.10% by weight of formic acid based on formaldehyde and when stored at 50°C about 2% by weight of formic acid after 10 days.

It is known that the formic acid can be removed by treating the formaldehyde solution with a basic ion exchanger (Walker, loc.cit., pages 29 to 31). This measure requires additional expensive apparatus, purification operations and expense for the ion exchanger used and for its regeneration. Since an ion exchanger should not be heated too much, the formaldehyde solution must not be too hot, and this in turn involves the risk of the formation of paraformaldehyde.

It is also known that the solution can be kept cool during storage to avoid the formation of formic acid; this results in the separation of paraformaldehyde. The solution may even thicken into a paste which can no longer be conveyed by pumps.

When solutions of formaldehyde containing formic acid are neutralized by adding amines or ammonia, the solutions obtained show very marked separation of polymerized formaldehyde which can no longer be processed.

It is known from Austrian Pat. No. 218,492 that ammonia and amines are catalyst poisons for the silver catalyst in the synthesis of formaldehyde.

This invention has for its object a new process for producing formaldehyde by a simpler and more economical method in good yields and with a lower content of formic acid.

U.S. Pat. No. 2,488,363 teaches that formaldehyde solutions are stabilized by adding to them phosphoric acid and phosphates, if desired together with primary aliphatic amines and hydroxyalkylamines of up to four carbon atoms and hexamethylenetetramine. In column 5, lines 70 to 75 reference is made to the fact that secondary and tertiary amines are of relatively little effect as compared with primary amines.

We have now found that formaldehyde is advantageously obtained by oxidizing dehydrogenation of methanol in the presence of a silver catalyst at elevated temperature when the reaction is carried out in the presence of from 0.00003 to 0.0005 mole, per mole of methanol, of amine of the general formula:

$$R^1-N-R^2 \atop | \atop R^3 \qquad (I)$$

in which $R^1$, $R^2$ and $R^3$ are identical or different aliphatic, cycloaliphatic or araliphatic radicals, $R^1$ may also be hydrogen, and $R^2$ and $R^3$ together with the adjacent nitrogen atom may be members of a heterocyclic ring.

The process of the invention gives formaldehyde in a good yield and with a substantially smaller content of formic acid by a simpler and more economical method than the prior art methods. The aqueous solutions of formaldehyde are more stable in storage and are devoid of formic acid or contain the acid in an amount less than 0.003% by weight based on formaldehyde. The acid concentration as a rule increases by less than 0.00035% by weight during storage for 10 days at 50° C. Salts of formic acid are also not contained in appreciable amounts in the formaldehyde solutions according to the invention. Amines bearing two or three substituents on the nitrogen atom are effective as catalysts, but not ammonia or primary amines, although for example dimethylamine and monomethylamine have the same basicity and should have similar neutralization action. Methylamine and ammonia are inactive even in 50% excess based on the formic acid present prior to the addition, whereas trimethylamine, which is of weaker basicity, is a suitable catalyst.

Since amines react with formaldehyde (Walker, loc. cit., pages 359 et seq), a loss of end product by reaction with formaldehyde was to be expected. Surprisingly, the process of the invention does not exhibit such loss to an appreciable extent.

The silver catalyst is extremely sensitive to impurities in the raw materials. Its life is shortened considerably by contamination of the crude feed methanol by for example alkali. It is therefore surprising having regard to the prior art that the catalytic effectiveness of the catalyst is not decreased by the amine. The addition of amine in the process according to the invention similarly does not have a polymerizing effect on the formaldehyde.

Formaldehyde solutions prepared by the process of the invention do not exhibit the said secondary reactions or polymerizations to an appreciable extent during storage. All these advantageous properties of the process are surprising having regard to the prior art.

Suitable starting materials for the process are pure methanol, commercial methanol or advantageously mixtures of the same with water; the concentration of the aqueous mixtures may vary advantageously from 60 to 95% by weight, preferably between 70 and 90% by weight. Crude methanol which as a rule has been purified by the methods described in German Printed Applications Nos. 1,277,834 and 1,235,881 by treatment with oxidizing agents and/or alkalies may also be used.

Generally the methanol is supplied in the form of vapor and if desired mixed with recycle offgas and/or with inert gas to the reaction chamber. Nitrogen for example is suitable as an inert gas for the process.

The oxidizing agent used may be pure oxygen or also a gas containing free oxygen, particularly air. Oxygen and methanol are conveniently used in a molar ratio of from 0.3 to 0.6 mole, particularly 0.4 to 0.5 mole, of oxygen per mole of methanol, and methanol and air are conveniently used in a molar ratio of 1 mole of methanol to 1.4 to 2.9 moles of air. The oxidation may be carried out in the presence of from 1 to 2 moles, advantageously 1 to 1.65 moles, particularly 1.3 to 1.5 moles of offgas per mole of methanol. The total amount of water vapor and any offgas added in addition to air should not amount to more than 3.0 moles per mole of methanol.

Any silver catalyst is suitable for the process of the invention, for example those described in German Printed Application No. 1,231,229 and Ullmanns Encyklopadie der technischen Chemie, volume 7, pages 659 et seq. It is preferred to use two-bed silver catalysts, for example the catalysts specified in German Printed Application No. 1,294,360 and in German Patent (patent application No. P 19 03 197.1). The said publications are referred to as regards the production of the catalyst and the method of carrying out the reaction with this catalyst. A preferred embodiment of the process of the invention consists in carrying out the reaction in contact with a two-bed catalyst, the lower bed being from 15 to 40 mm, particularly from 20 to 30 mm, in thickness and consisting to the extent of at least 50% of crystals of a particle size of from 1 to 4 mm, particularly from 1 to 2.5 mm, and the upper bed having a thickness of from 0.75 to 3 mm, particularly from 1 to 2 mm, and consisting of crystals of particle sizes of from 0.1 to 1 mm, particularly 0.2 to 0.75 mm, and using space velocities of from 1 to 3 metric tons, particularly 1.4 to 2.4 tons, of methanol per m² of catalyst bed cross-section per hour. For commercial operation it is preferred to use catalyst bed diameters of at least 0.5 meter, advantageously of from 1 meter to 3 meters.

The oxidation is otherwise carried out by conventional methods, for example by passing a gas mixture of methanol vapor, air, if desired inert gas, offgas and advantageously steam in the abovementioned amounts at temperatures of from about 550° to 780° C, particularly from 640° to 750° C, through the silver catalyst. It is advantageous to cool the reaction gas leaving the catalyst zone within a short time, for example in less than 0.2 second, for example to a temperature of from 50° to 160° C. The cooled gas mixture is then advantageously supplied to an absorber in which the formaldehyde is washed from the gas mixture with water, advantageously countercurrent. Some of the remaining offgas may then be allowed to escape and the remainder is advantageously recycled to the reaction.

The process is generally carried out at pressures of from 0.5 to 2 atmospheres, preferably from 0.8 to 1.8 atmospheres, batchwise or preferably continuously.

The proportion of offgas which is advantageously recycled to the reaction is from 1 to 2, preferably 1.3 to 1.5, moles per mole of methanol supplied to the reaction. The offgas contains mainly nitrogen, hydrogen, carbon dioxide, carbon monoxide, water, methanol, argon and as a rule from 0.1 to 0.5 gram of formaldehyde per cubic meter of offgas. It is advantageously treated with a basic compound — advantageously in an amount such that a pH of at least 10 and preferably from 11 to 13.5 is set up — and/or an oxidizing agent, then advantageously mixed with the other components of the starting mixture and then resupplied to the reactor. The basic compounds may preferably be alkalies such as solid or aqueous solutions of hydroxides, oxides or carbonates of the alkali metals or alkaline earth metals or other substances having an alkaline reaction, for example also organic alkali metal compounds such as alcoholates and phenolates, strongly basic amines usually of high boiling point such as triethanolamine. Aqueous caustic potash or caustic soda solutions are preferred for reasons of economy. Examples of oxidizing agents are hydrogen peroxide, sodium peroxide in aqueous solution; peroxomonosulfuric and peroxodisulfuric acid, perborates, percarbonates, organic peroxides and peroxyacids such as diacetyl peroxide and benzoic peracid, advantageously mixed with water; potassium permanganate or chromic acid, preferably in the form of aqueous 0.5 to 10% by weight solutions; and ozone. For reasons of economy and ease of operation hydrogen peroxide and potassium permanganate are preferred. From 0.02 to 10 g of oxidizing agent based on 1 cubic meter of offgas is generally used. The treatment is generally carried out continuously at a temperature of from 20° to 150° C, preferably from 30° to 70° C, at atmospheric or superatmospheric pressure. In a preferred embodiment the offgas is passed through a scrubber in which it is washed with a solution which contains the basic compound and/or oxidizing agent. The residence time is generally from 0.5 second to 15 seconds, but may amount to 2 minutes according to the oxidizing agent used. In continuous operation from 0.06 to 100, preferably from 0.08 to 1, g of basic compound and/or 0.02 to 10, preferably from 0.03 to 1, g of oxidizing agent (based on 1 cubic meter (STP) of offgas) is advantageously supplied to the treatment in the form of an aqueous solution of a strength of from 0.001 to 10, preferably 0.003 to 1% by weight. Instead of using the two treatment agents in combination, they may also be used singly. A two-stage treatment with both components, preferably first with the basic compound and then with the oxidizing agent, is also possible.

The reaction is carried out in the presence of from 0.00003 to 0.0005 mole, preferably from 0.00007 to 0.0001 mole, of amine based on 1 mole of methanol (calculated as 100%). The 28 to 65%, preferably 36 to 55%, by weight aqueous formaldehyde solutions containing the end product advantageously contain from 0.000032 to 0.00060 mole, particularly 0.00008 to 0.00012 mole, of amine based on 1 mole of formaldehyde (calculated as 100%). The amine is the starting amine and the nitrogen compounds contained in the solutions are accordingly calculated as amine 100%, disregarding their actual constitution, for example that of a decomposition product or condensation product of the starting amine.

Preferred amines are those of the general formula (I) in which $R^1$, $R^2$ and $R^3$ are identical or different alkyls of one to six carbon atoms, cyclohexyl, or aralkyls of seven to 12 carbon atoms, $R^1$ may also be hydrogen, and $R^2$ and $R^3$ may together with the adjacent nitrogen atom also be members of a five-membered or six-membered heterocyclic ring which may also contain another nitrogen atom. The said radicals and rings may also bear groups which are inert under the reaction conditions, for example hydroxyalkyl groups, alkyl groups, alkoxy groups each of one to four carbon atoms, and preferably an alkylamino group or a dialkylamino group of one to four carbon atoms per alkyl. Amines having a boiling point of from −10° to +200° C, preferably from −10° to +80° C, are advantageously used.

The following are examples of suitable amines: N,N-dimethylamine, N,N-diethylamine, N,N-diisobutylamine, N,N,N-triethoxyethylamine, N,N-methylcyclohexylamine, Δ2-pyrroline, Δ3-pyrroline, piperazine, imidazolidine, piperidine, pyrrolidine, N,N,N-trimethylamine, N,N'-dimethylethylenediamine, pyrazolidine, indoline, quinuclidine, tri-tert-butylamine, N,N-methylethylamine, di-n-propylamine, dibenzylamine, N,N-benzylethylamine, dicyclohexylamine, N,N,N-cyclohexyldimethylamine, N,N,N-benzyldiethylamine, N-methylpiperidine, N,N,N',N'-tetramethoxyethylethylenediamine, diethanolamine and triethanolamine.

The amines may be used in pure form or in solution and solvents which are inert under the reaction conditions may be used such as water; alkanols, for example ethanol or preferably methanol; or appropriate mixtures. Generally solutions of 20 to 60% by weight of amine are used. Mixtures of amines may also be used. The temperature of the amine solution or of the amine is advantageously at from 20° to 80° C. The amine may be added to the starting mixture in the vaporizer into which the water supplied is metered or it may be introduced into the vaporizer together with air or with the methanol. It is convenient to pump the amine or amine solution onto the boiling liquid in the vaporizer or into the evaporating liquid in circulation.

The formaldehyde which can be prepared by the process of the invention is a disinfectant, tanning agent, reducing agent and valuable starting material for the production of synthetic resins, adhesives and plastics. Reference is made to the said volume of Ullmann, page 670, as regards uses of formaldehyde.

The following Examples illustrate the invention. The parts specified are parts by weight.

EXAMPLE 1

A mixture of water and an 82% by weight aqueous crude methanol is boiled. The total amount of water is 310 parts and the total amount of methanol is 461 parts. 550 parts of air and 0.25 part of an aqueous 40% by weight dimethylamine solution are mixed with the boiling mixture. The vapor mixture formed is passed at 690° C and 1.4 atmospheres total pressure for 0.004 second over a bed of finely divided silver (particles having a diameter of about 1 mm), cooled to 150° C and dissolved in 90 parts of water in a scrubber. A mixture of 380 parts of formaldehyde, 570 parts of water, 17 parts of methanol and 0.002 part of formic acid is obtained.

EXAMPLE 2

(Comparative experiment)

The reaction is carried out as described in Example 1 but without adding dimethylamine. 379 parts (82.3% of theory based on methanol used) of formaldehyde and 0.102 part of formic acid are obtained.

EXAMPLE 3

200 parts of water, 300 parts of pure methanol, 520 parts of air and 0.16 part of a 38% by weight aqueous solution of dimethylamine are mixed, evaporated and passed at 1.08 atmospheres total pressure over a bed of silver 1 cm in thickness and consisting of particles of a diameter of 0.2 to 1 mm at 650° C. The mixture is cooled to 54° C and dissolved in a scrubber with an addition of 300 parts of water to form a 30.6% by weight formaldehyde solution. A mixture of 248 parts of formaldehyde, 564 parts of water and 11.7 parts of methanol is obtained. Formic acid cannot be detected.

EXAMPLE 4

In the manner described in Example 3, the reaction is carried out continuously while supplying the said starting mixture with 0.07 part per hour of dimethylamine as the amine. 248 parts (82.7% of theory) per hour of formaldehyde is obtained. After 2 hours of continuous operation formic acid is no longer detectable.

EXAMPLE 5

As described in Example 3 the reaction is carried out with 0.12 part of diisobutylamine. 250 parts (83.3% of theory) of formaldehyde and 0.0011 part of formic acid are obtained.

EXAMPLE 6

In the manner described in Example 3 the reaction is carried out with 0.14 part of piperidine. 247 parts (82.3% of theory) of formaldehyde and 0.0008 part of formic acid are obtained.

EXAMPLE 7

The reaction is carried out in the manner described in Example 3 with 0.22 part of a 40% by weight aqueous trimethylamine solution. 247 parts (82.3% of theory) of formaldehyde and 0.0010 part of formic acid are obtained.

EXAMPLE 8

1000 parts of a 40% by weight aqueous formaldehyde solution (the end product of Example 3) is kept at 50° C. Twenty-three days later the formic acid content is 0.040 part. If a solution of the same concentration not prepared according to the process of the invention is kept under the same conditions, 0.16 part is obtained.

EXAMPLE 9

A mixture of water and a 74% by weight aqueous crude methanol is boiled. The total amount of water is 455 parts and the total amount of methanol is 597 parts. 708 parts of air and 0.15 part of pyrrolidine is mixed with the boiling mixture. The vapor mixture formed is passed at 680° C and 1.25 atmospheres for 0.0045 second over a two-bed silver catalyst (as described in German Printed Application No. 1,231,229). The catalyst consists of a lower bed having a thickness of 20 mm of silver of a particle size of from 1.5 to 3 mm and an upper bed having a thickness of 1 mm of a particle size of from 0.2 to 1 mm. The space velocity is 1.9 metric tons of methanol per m² of the cross-section of the catalyst per hour. The reaction mixture is cooled to 150° C and dissolved in 135 parts of water in a scrubber. A mixture of 492 parts of formaldehyde, 738 parts of water, 16 parts of methanol and 0.001 part of formic acid is obtained.

We claim:

1. In a process for the production of formaldehyde by oxidizing dehydrogenation of methanol in the presence of a silver catalyst at 550° to 780° C the improvement wherein the reaction is carried out in the presence of from 0.00003 to 0.00050 mole, per mole of methanol, of an amine selected from the group consisting of a dialkylamine having alkyl groups of 1–6 carbon atoms, piperidine and pyrrolidone.

2. A process as claimed in claim 1 carried out in a molar ratio of 1 mole of methanol to 1.4 to 2.9 moles of air.

3. A process as claimed in claim 1 carried out at a pressure of from 0.5 to 2 atmospheres.

4. A process as claimed in claim 1 wherein said amount of said amine is in the range of 0.00007 to 0.0001 mol per mol of methanol.

5. A process as claimed in claim 1 wherein a vapor mixture of methanol, steam, gaseous oxygen and a solution of said amine are fed to a reactor containing a bed of said silver catalyst, and recovering the formaldehyde as an aqueous formaldehyde solution by absorption of the produced formaldehyde gas in water after passage of said vapor mixture through said bed of said silver catalyst, said aqueous formaldehyde solution containing less than 0.003% by weight, based on the formaldehyde, of formic acid.

* * * * *